United States Patent [19]
Sumi et al.

[11] Patent Number: 6,143,533
[45] Date of Patent: Nov. 7, 2000

[54] **METHOD FOR THE PREPARATION OF N-GLYCOLYL NEURAMINIC ACID FROM *CUCUMARIA ECHINATA***

[75] Inventors: Toshihisa Sumi, Tosu; Hideki Ohba, Kitakyushu; Toru Ikegami, Tosu; Masao Shibata, Ogoori; Tsuyoshi Sakaki, Tosu; Imre Sallay, Tosu; Sung Soo Park, Tosu, all of Japan

[73] Assignee: Agency of Industrial Science and Technology, Tokyo-To, Japan

[21] Appl. No.: 09/525,323

[22] Filed: Mar. 13, 2000

[30] Foreign Application Priority Data

Nov. 18, 1999 [JP] Japan .................................. 11-328316

[51] Int. Cl.⁷ ................................ C12P 7/40; C12P 7/58; A61K 35/12
[52] U.S. Cl. ........................ 435/136; 424/520; 424/572; 435/137
[58] Field of Search ..................................... 435/136, 137; 424/520, 572

[56] References Cited

U.S. PATENT DOCUMENTS 5,985,330  11/1999  Collin .

*Primary Examiner*—Leon B. Lankford, Jr.
*Attorney, Agent, or Firm*—Wenderoth, Lind & Ponack, L.L.P.

[57] ABSTRACT

Disclosed is an efficient and economical method for the preparation of N-glycolyl neuraminic acid in a high purity from an inexpensive abundant source material. The method comprises dispersing body tissues of an echinodermatous marine animal *Cucumaria echinata* in an aqueous medium, preferably, using a dry powder of the tissues prepared in advance, in which the tissues are proteolytically decomposed to isolate N-glycolyl neuraminic acid in the form of an aqueous solution containing polypeptides as a by-product, followed by separation of N-glycolyl neuraminic acid from the aqueous solution by removing the polypeptides and purification of the compound in a process utilizing an ion-exchange treatments.

5 Claims, 3 Drawing Sheets

METHOD FOR THE PREPARATION OF N-GLYCOLYL NEURAMINIC ACID FROM *CUCUMARIA ECHINATA*

BACKGROUND OF THE INVENTION

The present invention relates to a method for the preparation of N-glycolyl neuraminic acid. More particularly, the invention relates to an efficient and economical method for the preparation of N-glycolyl neuraminic acid from an inexpensive raw material of good availability as a hardly disposable waste material of nuisance discharged from fishery.

Acyl derivatives of neuraminic acid, having a generic name of sialic acids, are found at the non-reducing terminals of the molecules of certain complex saccharide compounds and play an important physiological role in living bodies. About 20 kinds of different sialic acids are known including those of which the N-acyl group is an N-acetyl group or N-glycolyl group and those of which the hydroxyl groups are substituted by acetyl groups or methyl groups.

According to the recent discovery relative to these sialic acids, N-glycolyl neuraminic acid is found in the living cells of human colorectal cancers and breast cancers though in a very small amount so that this compound is now becoming interested as a cancer marker.

It is the prior art that N-glycolyl neuraminic acid, which is used as a reference reagent in the analysis of saccharide compositions of a complex saccharide, is prepared by isolating and recovering from the tissues of vertebrate animals such as horses, cattle, pigs, dogs and the like. A problem in this supply route of the source material for the compound is that the content thereof in the living body tissues of the vertebrate animals is low and, in addition, difficulties are encountered in the purification of the compound isolated from the living body tissues necessarily leading to expensiveness of the commercial product. Moreover, the purity of the commercially available products of N-glycolyl neuraminic acid can hardly be higher than about 90%.

The inventors have conducted extensive investigations with an object to develop a novel and economical route for supplying N-glycolyl neuraminic acid including screening works to uncover a promising source material of the compound which can replace the vertebrate tissues, which have been the only source material of the compound in the prior art, and, directing their attention to a variety of materials occurring in nature, they have arrived at an unexpected discovery that certain marine animals well meet this purpose leading to establishment of the present invention after detailed studies on the processing procedure of the source material.

SUMMARY OF THE INVENTION

The primary object of the present invention is accordingly to provide a novel and efficient method for the preparation of N-glycolyl neuraminic acid by utilizing an inexpensive source material not utilized heretofore for the purpose.

The secondary object of the invention is to provide a method for the preparation of N-glycolyl neuraminic acid product having a high purity in a high yield not attained in any of the prior art methods starting from conventional vertebrate tissues.

Thus, the method of the present invention for the preparation of N-glycolyl neuraminic acid comprises the steps of:

(a) dispersing tissues of an echinodermatous marine animal having a zoological name of *Cucumara echinata* in an aqueous medium to form an aqueous suspension;

(b) proteolytically decomposing the tissues of the marine animal by the addition of a protease to the aqueous suspension to give an aqueous solution of N-glycolyl neuraminic acid isolated and solubilized by proteolytic decomposition containing polypeptides as a by-product;

(c) removing the polypeptides from the aqueous solution of N-glycolyl neuraminic acid; and (d) separating the N-glycolyl neuraminic acid from the aqueous medium.

DETAILED DESCRIPTION OF THE PREFERRED EMBODIMENTS

Figure 1:
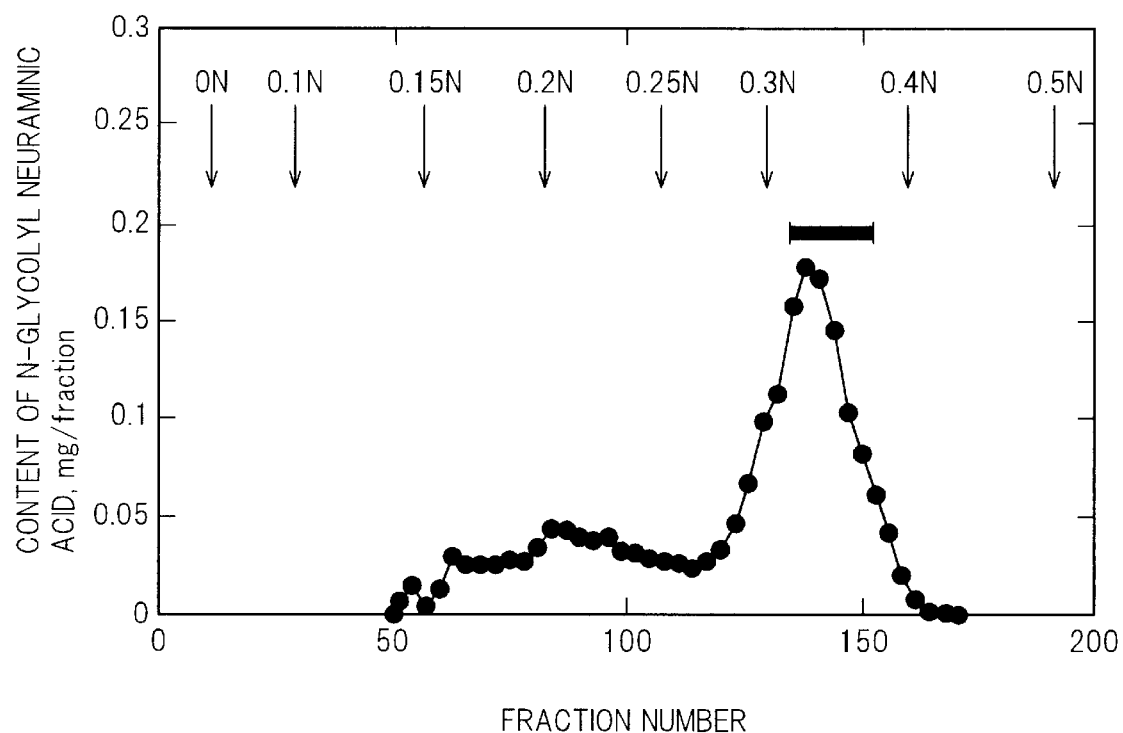
FIG. 1 is an elution diagram showing the content of N-glycolyl neuraminic acid in the fractions obtained by ion-exchange chromatography (see Example).

The source material in the inventive method is the body of an echinodermatous marine animal having a zoological name of *Cucumaria echinata*, referred to as "gumi" hereinafter by the Japanese trivial name, which is a kind of inedible sea cucumbers having a body length of several centimeters and living abundantly in the near seas around Japan. Gumi is so noxious against coast fishery to cause various damages that it is important to catch and remove gumi by using a fishing net as frequently as possible to clean the fishing sea area. A serious problem in this way of elimination of gumi is that absolutely no usefulness is known of the thus collected bodies of gumi so that the only way of disposal of gumi bodies is to bury the bodies under ground disregarding the possible troubles due to secondary environmental pollution caused thereby. Accordingly, bodies of gumi can be obtained in any large quantities at very low costs to be used as the starting raw material in the inventive method.

It is the inventors' discovery that the body tissues of gumi contain a relatively large amount of N-glycolyl neuraminic acid in a combined form so that tissues of gumi could be utilized as a source material for the preparation of N-glycolyl neuraminic acid so that the desired compound in a high purity could be obtained at low costs if an appropriate method be developed for isolation and recovery of the compound therefrom in a high purity.

As is described above, the scope of the inventive method relates to a process in which tissues of gumi dispersed in an aqueous medium are proteolytically decomposed to isolate N-glycolyl neuraminic acid giving an aqueous solution of the compound and the desired compound is separated from the aqueous solution. In particular, a convenient way therefor is that tissues of gumi are ground or homogenized in advance followed by drying to give a dry powder of the tissues to be stored, an appropriate portion of which is dispersed in an aqueous medium to give an aqueous suspension. The tissues of gumi in the aqueous suspension are proteolytically decomposed to isolate N-glycolyl neuraminic acid in the form of an aqueous solution containing polypeptides as a by-product, from which the polypeptides are removed by an ion-exchange treatment with a cation-exchange resin of the H+-form followed by separation of the desired compound from the aqueous solution.

In the preparation of an aqueous suspension of gumi tissues, namely, it is convenient and preferable that a dry powder of gumi bodies is prepared and stored in advance and the powder is employed in portions in the preparation of an aqueous suspension.

It is preferable in the preparation of a dry powder of gumi tissues that the living body tissues of gumi are ground or homogenized in an organic solvent such as acetone, petroleum ether and chloroform to give a slurry which is subjected to filtration or centrifugal separation to collect the solid matter followed by drying of the solid material under reduced pressure. The amount of the organic solvent is in the range from 10 to 30 times by weight relative to the wet amount of the gumi tissues. The yield of the thus dried gumi tissue powder is usually in the range from 80 to 150 g per 1000 g of the living body tissues of gumi.

In the next place, the dry powder of gumi tissues is added to an aqueous medium to give an aqueous suspension to be enzymatically solubilized therein. The amount of the aqueous medium used here is in the range from 3 to 6 times by weight relative to the amount of the dry powder. It is preferable that the aqueous medium is buffered to have a pH of 7.4 to 8.0 by the addition of calcium acetate and a tris buffer solution.

The aqueous suspension of gumi tissue powder is admixed with a protease such as Actinase to effect the proteolytic reaction so that the gumi tissue powder is solubilized. This proteolytic reaction is complete usually within 3 to 20 hours at an incubation temperature of 30 to 40° C., though widely dependent on the activity of the enzyme employed.

After completion of the proteolytic reaction, the aqueous suspension is heated at 100° C. to deactivate the protease and subjected to filtration or centrifugation to remove the solid matter. The clear filtrate or supernatant obtained is then subjected to a dialysis treatment against water and the solution after the dialysis treatment is brought into contact with a cation-exchange resin in the $H^+$-form to remove the polypeptides as a by-product of the proteolytic reaction to isolate N-glycolyl neuraminic acid followed by neutralization of the aqueous solution with an alkali. The neutralized aqueous solution of N-glycolyl neuraminic acid thus freed from impurities and by-products is concentrated by evaporating a part of water and then freeze-dried to give a pale brown powder which is N-glycolyl neuraminic acid in a crude form, which can be purified in the following manner.

Thus, the crude powder of N-glycolyl neuraminic acid is dissolved in an acidic aqueous solution and the aqueous solution is heated to effect hydrolysis of the compound followed by an ion-exchange treatment with a cation-exchange resin. The thus cation-exchange treated aqueous solution is then brought into contact with an anion-exchange resin so as to have N-glycolyl neuraminic acid adsorbed on the ion-exchange resin. In this way of purification, N-glycolyl neuraminic acid having a purity of 99% or higher can be obtained in a yield of 0.5 to 1.0% by weight based on the amount of the starting gumi tissues.

The gas chromatographic-mass spectrometric assay of the thus obtained N-glycolyl neuraminic acid gives a result just identical with that obtained for an authentic standard sample of the same compound.

In the following, the method of the present invention is described in more detail by way of an Example.

EXAMPLE (1) Preparation of a dry powder of gumi tissues

A slurry of gumi tissues was prepared by homogenizing 1300 g of living body tissues of gumi in 20 liters of acetone by using a homogenizer and the slurry was filtered under suction to collect the solid material which was dried under reduced pressure to give 131 g of a dry powder which contained about 0.15% by weight of N-glycolyl neuraminic acid.

(2) Preparation of an aqueous solution from gumi tissue powder

A 46.9 g portion of the above obtained gumi tissue powder was suspended in 200 ml of a 0.05M tris buffer solution having a pH of 7.8 containing 0.02M of calcium acetate to give an aqueous suspension to which 700 mg of a protease (Actinase E, a product by Kaken Seiyaku Co.) were added. The aqueous suspension was incubated at 37° C. for 48 hours to solubilize the gumi tissue powder followed by heating at 100° C. for 5 minutes to deactivate the enzyme. The aqueous suspension was then subjected to centrifugation at 20000 G for 40 minutes to settle the insoluble matter. The clear supernatant obtained by centrifugation was subjected to a dialysis treatment against distilled water and the dialyzed aqueous solution was passed through a 5×5 cm column filled with a cation-exchange resin (Dowex 50-x8, a product by Dow Chemical Co.) in the $H^+$-form to remove the polypeptides isolated from the gumi tissues as a by-product. The effluent was neutralized with sodium hydroxide and concentrated by evaporation of a part of water in a freeze-drying process. The concentrated aqueous solution was again subjected to a dialysis treatment against distilled water and freeze-dried to give 5.3 g of a crude product of N-glycolyl neuraminic acid.

(3) Purification

A 1.6 g portion of the crude product of N-glycolyl neuraminic acid obtained in (2) described above was dissolved in 500 ml of a 0.15N aqueous solution of trifluoroacetic acid and the solution was heated at 80° C. for 5 hours to effect hydrolysis of the compound. The solution obtained by the hydrolysis reaction was, after neutralization with sodium hydroxide, passed through a 5×5 cm ion-exchange column filled with a cation-exchange resin (Dowex 50-x8, supra) in the $H^+$-form and the effluent was, after neutralization with sodium hydroxide, concentrated by evaporating a part of water in a freeze-drying process. The concentrated aqueous solution was passed through a 1.5×32 cm ion-exchange column filled with an anion-exchange resin (Dowex 1-x8, a product by Dow Chemical Co.) in the formic acid-form to have the N-glycolyl neuraminic acid adsorbed on the resin as the adsorbent. The resin in the column was washed by passing distilled water in a volume of three times of the column volume to be freed from any unadsorbed solutes. Thereafter, elution of the adsorbed N-glycolyl neuraminic acid was conducted with an aqueous solution of formic acid in a volume of three times of the column volume, of which the formic acid concentration was stepwise increased from 0.1N to 0.5N to collect the eluate solution in a plurality of fractions each in a volume of 4.65 ml. Each of the fractions was analyzed for the content of N-glycolyl neuraminic acid to give the results shown in FIG. 1 which is an elution diagram showing the content of the compound in each of the fractions. The fractions corresponding to the formic acid concentration in the eluant of 0.3N to 0.4N were collected together and subjected to freeze-drying to give 11.1 mg of purified N-glycolyl neuraminic acid corresponding to a 52% yield based on the content in the dried gumi tissue powder. The normality figure on each of the downward arrows in FIG. 1 is the concentration of formic acid in the eluant solution.

(4) Assay

Each a 30 μg portion of the purified N-glycolyl neuraminic acid obtained above and an authentic monosaccharide mixture of NeuGc and NeuAc (a product by Sigma Co.) were each admixed with 6 μg of myoinositol as an internal standard and kept in a desiccator of phosphorus pentoxide until absolute dryness. Each of the thus dried mixtures was added to 1 ml of a 0.025N hydrogen chloride solution in methyl alcohol and the solution was kept at 70° C. for 30 minutes to effect the reaction. The reaction mixture was freed from hydrogen chloride and methyl alcohol by blowing nitrogen gas at the surface followed by a trimethylsilylation reaction for 30 minutes with addition of a silylating agent to convert the sample compound into a silylated derivative having vaporizability.

The thus obtained vaporizable derivative compounds were each subjected to gas chromatographic-mass spectrometric analysis on a gas chromatograph-mass spectrometer (Model QP-5000, manufactured by Shimadzu Seisakusho Co.) equipped with a 0.25 mm×30 m capillary column CBP-1. The temperature elevation program of the gas chromatographic column was such that a temperature of 40° C. was kept for 3 minutes followed by temperature elevation first at a rate of 20° C./minute up to 180° C. and thereafter at a rate of 1.5° C./minute up to 240° C. The ionization source of the mass spectrometer was of the electron-bombardment type and mass spectrometric measurement was conducted with an ionization potential of 70 eV, ionization source temperature of 220° C. and scanning interval of 0.5 second. The internal standard method was employed for the quantitative determination of N-glycolyl neuraminic acid. The gas chromatogram and the mass spectrum obtained in this analysis are shown in FIGS. 2 and 3, respectively.

Figure 2:
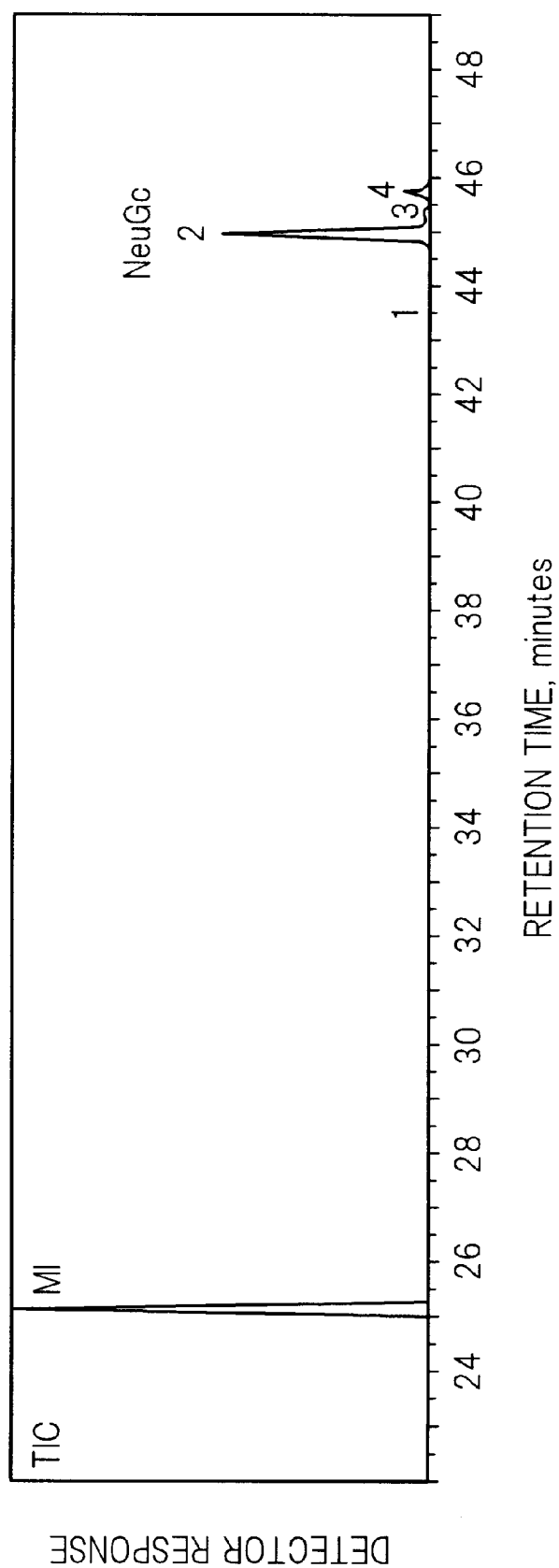
FIG. 2 is a gas chromatographic pattern of purified N-glycolyl neuraminic acid obtained according to the inventive method.

The gas chromatogram shown in FIG. 2 indicates four peaks NeuGlc 1, 2, 3 and 4 which can be correlated to N-glycolyl neuraminic acid. The retention times of these four peaks relative to that of myoinositol (peak MI) were each in perfect coincidence with those of the corresponding peaks obtained for the authentic sample of N-glycolyl neuraminic acid (a product by Sigma Co.).

Figure 3:
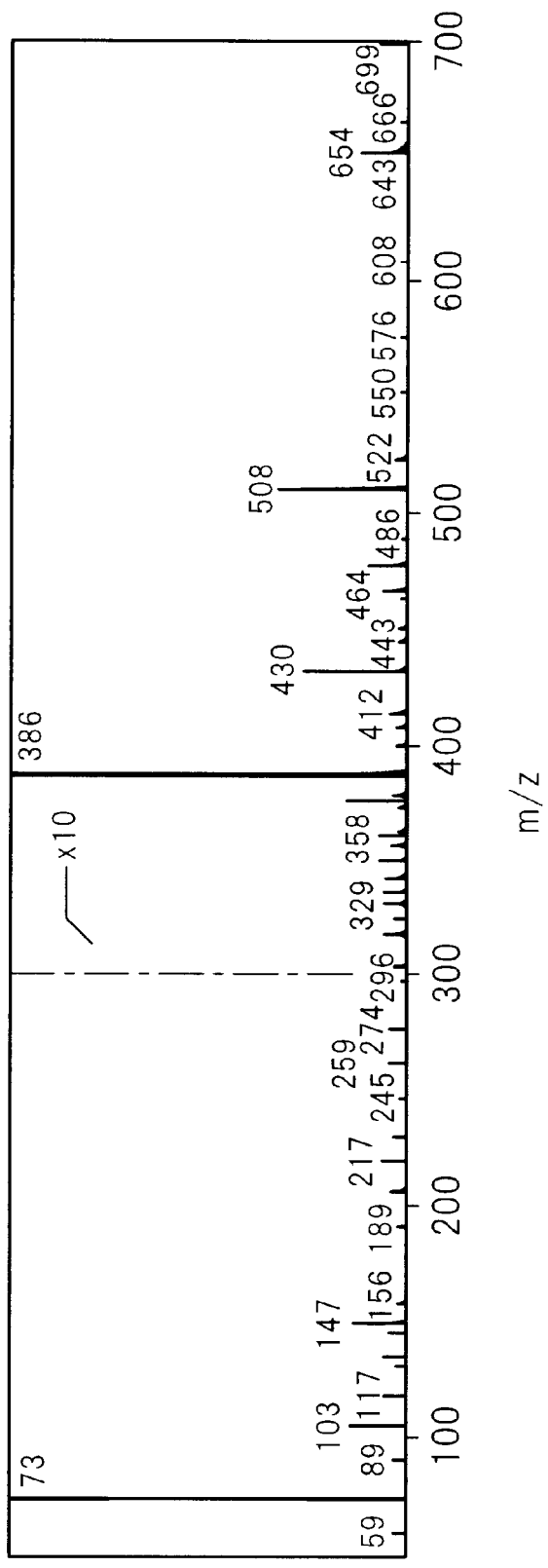
FIG. 3 is a mass spectrometric spectrum of N-glycolyl neuraminic acid obtained by the inventive method.

In the mass spectrum shown in FIG. 3, the relative intensity ratio of the principal peaks corresponding to the ions of mass numbers (m/z) of 654, 508, 430 and 386 was in perfect coincidence with the ratio obtained for the same authentic sample as used above.

The above described results of the identification tests of the product obtained by the inventive method definitely support the conclusion that the product is N-glycolyl neuraminic acid in a purity of 99.19%, the balance of 0.81% being N-acetyl neuraminic acid as an impurity.

What is claimed is:

1. A method for the preparation of N-glycolyl neuraminic acid which comprises the steps of:

(a) dispersing tissues of an echinodermatous marine animal having a zoological name of *Cucumara echinata* in an aqueous medium to form an aqueous suspension;

(b) proteolytically decomposing the tissues of the echinodermatous marine animal by the addition of a protease to the aqueous suspension to give an aqueous solution of N-glycolyl neuraminic acid isolated and solubilized by proteolytic decomposition containing polypeptides as a by-product;

(c) removing the polypeptides from the aqueous solution of N-glycolyl neuraminic acid; and (d) separating the N-glycolyl neuraminic acid from the aqueous solution.

2. The method for the preparation of N-glycolyl neuraminic acid as claimed in claim 1 in which the aqueous suspension of the tissues of the echinodermatous marine animal is prepared by dispersing a dry powder of the tissues in the aqueous medium.

3. The method for the preparation of N-glycolyl neuraminic acid as claimed in claim 1 in which the step (c) for removing the polypeptides from the aqueous solution of N-glycolyl neuraminic acid is carried out by bringing the aqueous solution into contact with a cation-exchange resin in the $H^+$-form.

4. The method for the preparation of N-glycolyl neuraminic acid as claimed in claim 1 in which the aqueous medium, in which the tissues of the echinodermatous marine animal is dispersed in step (a), has a pH in the range from 7.4 to 8.0 as buffered with a tris buffer solution and calcium acetate.

5. The method for the preparation of N-glycolyl neuraminic acid as claimed in claim 1 in which the proteolytic decomposition of the tissues is carried out at a temperature in the range from 30 to 40° C. for 3 to 20 hours.

* * * * *

UNITED STATES PATENT AND TRADEMARK OFFICE
CERTIFICATE OF CORRECTION

PATENT NO. : 6,143,533
DATED : November 7, 2000
INVENTOR(S) : Toshihisa SUMI et al.

It is certified that error appears in the above-identified patent and that said Letters Patent is hereby corrected as shown below:

On the cover page, the Assignnee information should read: --Japan as represented by Secretary of Agency of Industrial Science and Technology, Tokyo-to, JAPAN.--.

Column 1, line 66, change "*Cucumara*" to --*Cucumaria*--.

Column 6, line 8, change "*Cucumara*" to --*Cucumaria*--.

Signed and Sealed this

First Day of May, 2001

Attest:

NICHOLAS P. GODICI

*Attesting Officer*   *Acting Director of the United States Patent and Trademark Office*